(12) United States Patent
Davis et al.

(10) Patent No.: US 6,906,048 B2
(45) Date of Patent: Jun. 14, 2005

(54) N-ACETYLCOLCHINOL-O-PHOSPHATE COMBINATION THERAPIES WITH VASCULAR DAMAGING ACTIVITY

(75) Inventors: Peter David Davis, Oxford (GB); Graeme Dougherty, Los Angeles, CA (US)

(73) Assignee: AstraZeneca AB, Sodertalje (SE)

( * ) Notice: Subject to any disclaimer, the term of this patent is extended or adjusted under 35 U.S.C. 154(b) by 22 days.

(21) Appl. No.: 10/240,213

(22) PCT Filed: Mar. 27, 2001

(86) PCT No.: PCT/GB01/01317

§ 371 (c)(1),
(2), (4) Date: Apr. 4, 2003

(87) PCT Pub. No.: WO01/74368

PCT Pub. Date: Oct. 11, 2001

(65) Prior Publication Data

US 2003/0166617 A1 Sep. 4, 2003

(30) Foreign Application Priority Data

| Mar. 31, 2000 | (GB) | 0007740 |
| Jun. 8, 2000 | (GB) | 0013927 |
| Jun. 20, 2000 | (GB) | 0014908 |

(51) Int. Cl.[7] .................. A61K 31/661; A61K 31/337; A61K 31/282
(52) U.S. Cl. .............. 514/119; 514/449; 514/184
(58) Field of Search ............... 514/104, 119, 514/184, 449

(56) References Cited

U.S. PATENT DOCUMENTS

2003/0055024 A1   3/2003  Davis .................... 514/114

FOREIGN PATENT DOCUMENTS

| WO | 99/02166 | 1/1999 |
| WO | 99/65515 | * 12/1999 |
| WO | 00/48591 A1 | 8/2000 |
| WO | 01/74369 A1 | 10/2001 |

OTHER PUBLICATIONS

Blakey et al., "Anti–tumour activity of the novel vascular targeting agent ZD6126 in a human lung tumour xenograft model", Clin. Cancer Res., CODEN: CCREF ISSN: 1078–0432, vol. 6, (SUPPL. 4522s, Abs. No. 283), Nov., 2000, XP000999407, AstraZeneca, abstract.

Siemann, D.W., "The novel vascular targeting agent ZD6126 enhances the antitumor treatment efficacy of cisplatin and radiotherapy", Clin. Cancer Res., CODEN: CCREF ISSN: 1078–0432, vol. 6 (SUPPL., 4522s, Abs. No. 284), Nov., 2000, XP000999406, University of Florida, abstract.

Siemann et al., "Targeting tumor blood vessels: An adjuvant strategy for radiation therapy", Radiotherapy and Oncology, (Oct. 1, 2000), 57/1 (5–12), CODEN: RAONDT ISSN: 067–8140, XP001007731, University of Florida, p. 6, column 2, line 9–line 11, table 1.

Davis et al., "Anti–tumour activity of vascular targeting agent ZD6126 is enhanced by split dosing", Clinical Cancer Res., CODEN CCREF ISSN: 1078–0432, vol. 6 (SUPPL., 4522s, Abs. No. 282) Nov., 2000, XP000999405, Angiogene Pharmaceuticals, abstract.

* cited by examiner

Primary Examiner—Phyllis Spivack
(74) Attorney, Agent, or Firm—Morgan, Lewis & Bockius LLP

(57) ABSTRACT

The invention relates to a method for the production of a vascular damaging effect in a warm-blooded animal such as a human, which comprises administering to said animal an effective amount of ZD6126 or a pharmaceutically acceptable salt thereof, before, after or simultaneously with an effective amount of one of the following therapies: i) ionizing radiation; ii) a platinum anti-tumor agent; and iii) a taxane. The invention also relates to the use of ZD6126 and one of the above therapies in the manufacture of a medicament for use in the production of a vascular damaging effect in a warm-blooded animal such as a human and to pharmaceutical compositions and kits each comprising ZD6126 and one of a platinum anti-tumor agent and a taxane

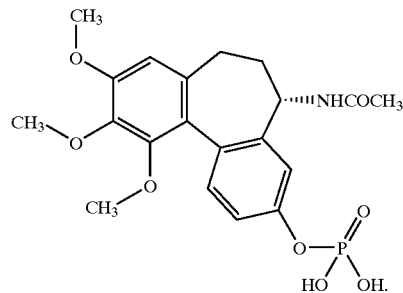

9 Claims, 9 Drawing Sheets

Figure 1:
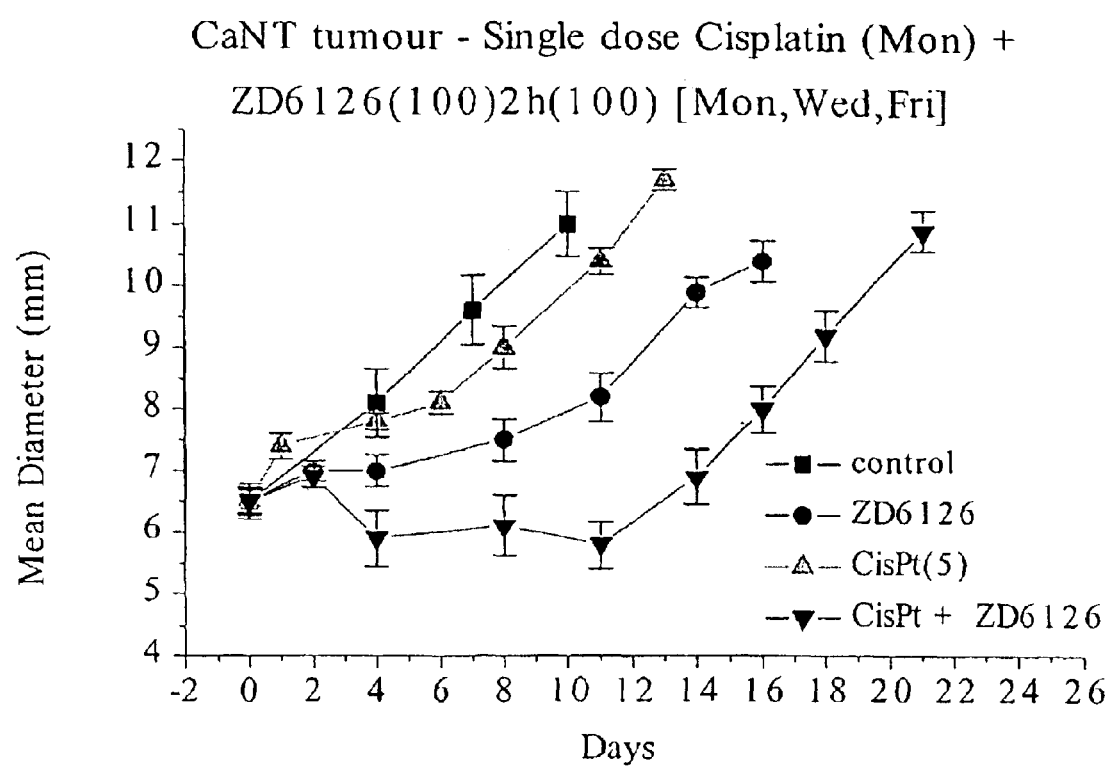

Hatched box is the tumour cell kill achieved with 10mg/kg cisplatin alone.

Radiation plus ZD6126 line represents the mean of 3 separate experiments.

N-ACETYLCOLCHINOL-O-PHOSPHATE COMBINATION THERAPIES WITH VASCULAR DAMAGING ACTIVITY

The present invention relates to a method for the production of a vascular damaging effect in a warm-blooded animal such as a human, particularly a method for the treatment of a cancer involving a solid tumour, which comprises the administration of ZD6126 in combination with one of: a platinum anti-tumour agent, a taxane or ionising radiation; to a pharmaceutical composition comprising ZD6126 and one of: a platinum anti-tumour agent and a taxane; to a combination product comprising ZD6126 and one of a platinum anti-tumour agent and a taxane for use in a method of treatment of a human or animal body by therapy; to a kit comprising ZD6126 and one of: a platinum anti-tumour agent and a taxane; to the use of ZD6126 and one of: a platinum anti-tumour agent and a taxane in the manufacture of a medicament for use in the production of a vascular damaging effect in a warm-blooded animal such as a human which is optionally being concomitantly treated with ionising radiation; and to the use of ZD6126 in the manufacture of a medicament for use in the production of a vascular damaging effect in a warm-blooded animal such as a human which is being treated with ionising radiation.

The present invention further relates to a method for the production of a vascular damaging effect in a warm-blooded animal such as a human, particularly a method for the treatment of a cancer involving a solid tumour, which comprises the administration of ZD6126 in divided doses, in combination with one of: a platinum anti-tumour agent, a taxane or ionising radiation; to a combination product comprising two or more doses of ZD6126 for administration in divided doses, and one of a platinum anti-tumour agent and a taxane, for use in a method of treatment of a human or animal body by therapy; to a kit comprising two or more doses of ZD6126 for administration in divided doses, and one of: a platinum anti-tumour agent and a taxane; to the use of ZD6126 in the manufacture of a medicament for use in divided doses for use in the production of a vascular damaging effect in a warm-blooded animal such as a human which is concomitantly treated with one of: a platinum anti-tumour agent and a taxane; to the use of ZD6126 in the manufacture of a medicament for use in divided doses in the production of a vascular damaging effect in a warm-blooded animal such as a human which is being concomitantly treated with ionising radiation.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is expected to have a beneficial therapeutic effect. International Patent Application No. PCT/GB98/01977 (Publication No. WO 99/02166) describes tricyclic compounds that surprisingly have a selective damaging effect on newly formed vasculature as compared to the normal, established vascular endothelium of the host species. This is a property of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

Compounds which damage newly formed vasculature are vascular damaging agents (VDAs) and are also known as vascular targeting agents (VTAs).

One compound described in International Patent Application No. PCT/GB98/01977 (Publication No. WO 99/02166) is N-acetylcolchinol-O-phosphate, (also know as (5S)-5-(acetylamino)-9,10,11-trimethoxy-6,7-dihydro-5H-dibenzo[a,c]cyclohepten-3-yl dihydrogen phosphate; Example 1 of International Patent Application No. PCT/GB98/01977 (Publication No. WO 99/02166)), which is referred to herein as ZD6126.

It is believed, though this is not limiting on the invention, that ZD6126 damages newly-formed vasculature, for example the vasculature of tumours, thus effectively reversing the process of angiogenesis. This may be compared with other known anti-angiogenic agents which tend to be less effective once the vasculature has formed.

In International Patent Application No. PCT/GB98/01977 (Publication No. WO 99/02166) it is stated that: "compounds of the invention may be administered as sole therapy or in combination with other treatments. For the treatment of solid tumours compounds of the invention may be administered in combination with radiotherapy or in combination with other anti-tumour substances for example those selected from mitotic inhibitors, for example vinblastine, paclitaxel and docetaxel; alkylating agents, for example cisplatin, carboplatin and cyclophosphamide, antimetabolites, for example 5-fluorouracil, cytosine arabinoside and hydroxyurea; intercalating agents for example adriamycin and bleomycin; enzymes, for example asparaginase; topoisomerase inhibitors for example etoposide, topotecan and irinotecan; thymidylate synthase inhibitors for example raltitrexed; biological response modifers for example interferon; antibodies for example edrecolomab, and anti-hormones for example tamoxifen. Such combination treatment may involve simultaneous or sequential application of the individual components of the treatment." Nowhere in International Patent Application No. PCT/GB98/01977 (Publication No. WO 99/02166) does it state that use of any compound of the invention therein with other treatments will produce surprisingly beneficial effects.

Unexpectedly and surprisingly we have now found that the particular compound ZD6126 used in combination with a particular selection of the combination therapies listed in International Patent Application No. PCT/GB98/01977 (Publication No. WO 99/02166), namely with one of: a platinum anti-tumour agent, a taxane and ionising radiation, produces significantly better effects on solid tumours than any one of ZD6126, a platinum anti-tumour agent, a taxane and ionising radiation used alone.

Anti-tumour effects of a method of treatment of the present invention include but are not limited to, inhibition of tumour growth, tumour growth delay, regression of tumour, shrinkage of tumour, increased time to regrowth of tumour on cessation of treatment, slowing of disease progression. It is expected that when a method of treatment of the present invention is administered to a warm-blooded animal such as a human, in need of treatment for cancer involving a solid tumour, said method of treatment will produce an effect, as measured by, for example, one or more of: the extent of the anti-tumour effect, the response rate, the time to disease progression and the survival rate.

According to another aspect of the present invention the effect of a method of treatment of the present invention is expected to be at least equivalent to the addition of the effects of each of the components of said treatment used alone, that is, of each of ZD6126 and one of: a platinum anti-tumour agent, a taxane and ionising radiation, used alone.

According to another aspect of the present invention the effect of a method of treatment of the present invention is expected to be greater than the addition of the effects of each of the components of said treatment used alone, that is, of each of ZD6126 and one of: a platinum anti-tumour agent, a taxane and ionising radiation, used alone.

Without being bound by theoretical considerations, it is particularly surprising that ZD6126 in combination with a taxane gives significantly better effects on solid tumours than ZD6126 or a taxane used alone. This is particularly surprising because taxanes promote assembly of microtubules and inhibit their depolymerisation to free tubulin, (The Merck Index 1996, $12^{th}$ Edition entry nos. 7117 and 3458 for paclitaxel and docetaxel respectively), and this would be expected to antagonise the damaging effect of ZD6126 on newly-formed vasculature instead of which, and unexpectedly, an enhanced anti-tumour effect is produced when ZD6126 is used in combination with a taxane.

Unexpectedly and surprisingly we have now found that ZD6126, when dosed in divided doses (also known as split doses) produces a greater anti-tumour effect than when a single dose of ZD6126 is given.

According to the present invention there is provided a method for the production of a vascular damaging effect in a warm-blooded animal such as a human, which comprises administering to said animal an effective amount of ZD6126:

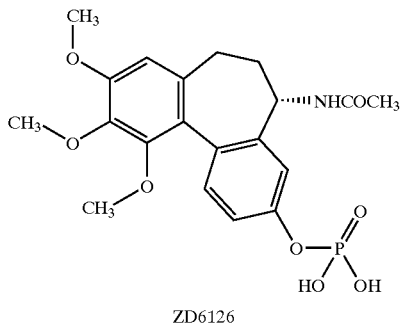

ZD6126 or a pharmaceutically acceptable salt thereof, before, after or simultaneously with an effective amount of one of the following therapies:
 i) ionising radiation;
 ii) a platinum anti-tumour agent; and
 iii) a taxane.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of ionising radiation.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of a platinum anti-tumour agent.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of a taxane.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of one of the following therapies:
 i) ionising radiation;
 ii) a platinum anti-tumour agent; and
 iii) a taxane.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of ionising radiation.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of a platinum anti-tumour agent.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of a taxane.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of one of the following therapies:
 i) ionising radiation;
 ii) a platinum anti-tumour agent; and
 iii) a taxane;
wherein ZD6126, a platinum anti-tumour agent and a taxane may each optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of ionising radiation wherein ZD6126 may optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of a platinum anti-tumour agent wherein ZD6126 and a platinum anti-tumour agent may each optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, before, after or simultaneously with an effective amount of a taxane wherein ZD6126 and a taxane may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of one of the following therapies:

i) ionising radiation;
ii) a platinum anti-tumour agent; and
iii) a taxane;

wherein ZD6126, a platinum anti-tumour agent and a taxane may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of ionising radiation wherein ZD6126 may optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of a platinum anti-tumour agent wherein ZD6126 and a platinum anti-tumour agent may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, before, after or simultaneously with an effective amount of a taxane wherein ZD6126 and a taxane may each optionally be administered together with a pharmaceutically acceptable excipient or carrier.

According to a further aspect of the invention there is provided a pharmaceutical composition which comprises ZD6126 or a pharmaceutically acceptable salt thereof, and a platinum anti-tumour agent in association with a pharmaceutically acceptable excipient or carrier.

According to a further aspect of the invention there is provided a pharmaceutical composition which comprises ZD6126 or a pharmaceutically acceptable salt thereof, and a taxane in association with a pharmaceutically acceptable excipient or carrier.

According to a further aspect of the present invention there is provided a combination product comprising ZD6126 or a pharmaceutically acceptable salt thereof and one of: a platinum anti-tumour agent and a taxane, for use in a method of treatment of a human or animal body by therapy.

According to a further aspect of the present invention there is provided a combination product comprising ZD6126 or a pharmaceutically acceptable salt thereof and a platinum anti-tumour agent, for use in a method of treatment of a human or animal body by therapy.

According to a further aspect of the present invention there is provided a combination product comprising ZD6126 or a pharmaceutically acceptable salt thereof and a taxane, for use in a method of treatment of a human or animal body by therapy.

According to a further aspect of the present invention there is provided a kit comprising ZD6126 or a pharmaceutically acceptable salt thereof, and one of: a platinum anti-tumour agent and a taxane.

According to a further aspect of the present invention there is provided a kit comprising ZD6126 or a pharmaceutically acceptable salt thereof, and a platinum anti-tumour agent.

According to a further aspect of the present invention there is provided a kit comprising ZD6126 or a pharmaceutically acceptable salt thereof, and a taxane.

According to a further aspect of the present invention there is provided a kit comprising:
a) ZD6126 or a pharmaceutically acceptable salt thereof in a first unit dosage form;
b) one of: a platinum anti-tumour agent and a taxane in a second unit dosage form; and
c) container means for containing said first and second dosage forms.

According to a further aspect of the present invention there is provided a kit comprising:
a) ZD6126 or a pharmaceutically acceptable salt thereof in a first unit dosage form;
b) a platinum anti-tumour agent in a second unit dosage form; and
c) container means for containing said first and second dosage forms.

According to a further aspect of the present invention there is provided a kit comprising:
a) ZD6126 or a pharmaceutically acceptable salt thereof in a first unit dosage form;
b) a taxane in a second unit dosage form, and
c) container means for containing said first and second dosage forms.

According to a further aspect of the present invention there is provided a kit comprising:
a) ZD6126 or a pharmaceutically acceptable salt thereof, together with a pharmaceutically acceptable excipient or carrier, in a first unit dosage form;
b) one of: a platinum anti-tumour agent and a taxane, together with a pharmaceutically acceptable excipient or carrier, in a second unit dosage form; and
c) container means for containing said first and second dosage forms.

According to a further aspect of the present invention there is provided a kit comprising:
a) ZD6126 or a pharmaceutically acceptable salt thereof, together with a pharmaceutically acceptable excipient or carrier, in a first unit dosage form;
b) a platinum anti-tumour agent together with a pharmaceutically acceptable excipient or carrier, in a second unit dosage form; and
c) container means for containing said first and second dosage forms.

According to a further aspect of the present invention there is provided a kit comprising:
a) ZD6126 or a pharmaceutically acceptable salt thereof, together with a pharmaceutically acceptable excipient or carrier, in a first unit dosage form;
b) a taxane together with a pharmaceutically acceptable excipient or carrier, in a second unit dosage form; and
c) container means for containing said first and second dosage forms.

According to a further aspect of the present invention there is provided the use of ZD6126 or a pharmaceutically acceptable salt thereof and one of: a platinum anti-tumour agent and a taxane, in the manufacture of a medicament for use in the production of a vascular damaging effect in a warm-blooded animal such as a human.

According to a further aspect of the present invention there is provided the use of ZD6126 or a pharmaceutically acceptable salt thereof and a platinum anti-tumour agent in the manufacture of a medicament for use in the production of a vascular damaging effect in a warm-blooded animal such as a human.

According to a further aspect of the present invention there is provided the use of ZD6126 or a pharmaceutically acceptable salt thereof and a taxane in the manufacture of a medicament for use in the production of a vascular damaging effect in a warm-blooded animal such as a human.

According to a further aspect of the present invention there is provided the use of ZD6126 or a pharmaceutically acceptable salt thereof and one of: a platinum anti-tumour agent and a taxane, in the manufacture of a medicament for use in the production of an anti-cancer effect in a warm-blooded animal such as a human.

According to a further aspect of the present invention there is provided the use of ZD6126 or a pharmaceutically acceptable salt thereof and a platinum anti-tumour agent in the manufacture of a medicament for use in the production of an anti-cancer effect in a warm-blooded animal such as a human.

According to a further aspect of the present invention there is provided the use of ZD6126 or a pharmaceutically acceptable salt thereof and a taxane in the manufacture of a medicament for use in the production of an anti-cancer effect in a warm-blooded animal such as a human.

According to a further aspect of the present invention there is provided the use of ZD6126 or a pharmaceutically acceptable salt thereof and one of: a platinum anti-tumour agent and a taxane, in the manufacture of a medicament for use in the production of an anti-tumour effect in a warm-blooded animal such as a human.

According to a further aspect of the present invention there is provided the use of ZD6126 or a pharmaceutically acceptable salt thereof and a platinum anti-tumour agent in the manufacture of a medicament for use in the production of an anti-tumour effect in a warm-blooded animal such as a human.

According to a further aspect of the present invention there is provided the use of ZD6126 or a pharmaceutically acceptable salt thereof and a taxane in the manufacture of a medicament for use in the production of an anti-tumour effect in a warm-blooded animal such as a human.

According to a further aspect of the present invention there is provided the use of ZD6126 or a pharmaceutically acceptable salt thereof in the manufacture of a medicament for use in the production of a vascular damaging effect in a warm-blooded animal such as a human which is being treated with ionising radiation.

According to a further aspect of the present invention there is provided the use of ZD6126 or a pharmaceutically acceptable salt thereof in the manufacture of a medicament for use in the production of an anti-cancer effect in a warm-blooded animal such as a human which is being treated with ionising radiation.

According to a further aspect of the present invention there is provided the use of ZD6126 or a pharmaceutically acceptable salt thereof in the manufacture of a medicament for use in the production of an anti-tumour effect in a warm-blooded animal such as a human which is being treated with ionising radiation.

A warm-blooded animal such as a human which is being treated with ionising radiation means a warm-blooded animal such as a human which is treated with ionising radiation before, after or at the same time as the administration of a medicament comprising ZD6126. For example said ionising radiation may be given to said warm-blooded animal such as a human within the period of a week before to a week after the administration of a medicament comprising ZD6126.

According to a further aspect of the present invention there is provided a combination treatment comprising the administration of an effective amount of ZD6126 or a pharmaceutically acceptable salt thereof, optionally together with a pharmaceutically acceptable excipient or carrier, and the simultaneous, sequential or separate administration of an effective amount of one of:
  i) ionising radiation;
  ii) a platinum anti-tumour agent; and
  iii) a taxane;
wherein a platinum anti-tumour agent and a taxane may each optionally be administered together with a pharmaceutically acceptable excipient or carrier;
to a warm-blooded animal such as a human in need of such therapeutic treatment. Such therapeutic treatment includes a vascular damaging effect, an anti-cancer effect and an anti-tumour effect.

According to a further aspect of the present invention there is provided a combination treatment comprising the administration of an effective amount of ZD6126 or a pharmaceutically acceptable salt thereof, optionally together with a pharmaceutically acceptable excipient or carrier, and the simultaneous, sequential or separate administration of an effective amount of ionising radiation to a warm-blooded animal such as a human in need of such therapeutic treatment.

According to a further aspect of the present invention there is provided a combination treatment comprising the administration of an effective amount of ZD6126 or a pharmaceutically acceptable salt thereof, optionally together with a pharmaceutically acceptable excipient or carrier, and the simultaneous, sequential or separate administration of an effective amount of a platinum anti-tumour agent, wherein a platinum anti-tumour agent may optionally be administered together with a pharmaceutically acceptable excipient or carrier, to a warm-blooded animal such as a human in need of such therapeutic treatment.

According to a further aspect of the present invention there is provided a combination treatment comprising the administration of an effective amount of ZD6126 or a pharmaceutically acceptable salt thereof, optionally together with a pharmaceutically acceptable excipient or carrier, and the simultaneous, sequential or separate administration of an effective amount of a taxane, wherein a taxane may optionally be administered together with a pharmaceutically acceptable excipient or carrier, to a warm-blooded animal such as a human in need of such therapeutic treatment.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of one of the following therapies:
i) ionising radiation;
ii) a platinum anti-tumour agent; and
iii) a taxane.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of ionising radiation.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of a platinum anti-tumour agent.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of a taxane.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of one of the following therapies:
i) ionising radiation;
ii) a platinum anti-tumour agent; and
iii) a taxane.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of ionising radiation.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of a platinum anti-tumour agent.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of a taxane.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of one of the following therapies:
i) ionising radiation;
ii) a platinum anti-tumour agent; and
iii) a taxane;
wherein ZD6126, a platinum anti-tumour agent and a taxane may each optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of ionising radiation wherein ZD6126 may optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of a platinum anti-tumour agent wherein ZD6126 and a platinum anti-tumour agent may each optionally be administered together with a pharmaceutically acceptable excipient or carrier.

According to a further aspect of the present invention there is provided a method for the production of a vascular damaging effect in a warm-blooded animal such as a human, which comprises administering to said animal an effective amount of ZD6126 or a pharmaceutically acceptable salt thereof, in divided doses, before, after or simultaneously with an effective amount of a taxane wherein ZD6126 and a taxane may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of one of the following therapies:
i) ionising radiation;
ii) a platinum anti-tumour agent; and
iii) a taxane;
wherein ZD6126, a platinum anti-tumour agent and a taxane may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of ionising radiation wherein ZD6126 may optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of a platinum anti-tumour agent wherein ZD6126 and a platinum anti-tumour agent may each optionally be administered together with a pharmaceutically acceptable excipient or carrier.

According to a further aspect of the present invention there is provided a method for the treatment of a cancer involving a solid tumour in a warm-blooded animal such as a human, which comprises administering to said animal an effective amount of ZD6126 or a pharmaceutically acceptable salt thereof, in divided doses, before, after or simultaneously with an effective amount of a taxane wherein ZD6126 and a taxane may each optionally be administered together with a pharmaceutically acceptable excipient or carrier.

According to a further aspect of the present invention there is provided a combination product comprising two or more fractions of doses of ZD6126 or a pharmaceutically acceptable salt thereof, which together add up to a total daily dose, for administration in divided doses, and one of: a platinum anti-tumour agent and a taxane, for use in a method of treatment of a human or animal body by therapy.

According to a further aspect of the present invention there is provided a combination product comprising two or more fractions of doses of ZD6126 or a pharmaceutically acceptable salt thereof, which together add up to a total daily dose, for administration in divided doses, and a platinum anti-tumour agent, for use in a method of treatment of a human or animal body by therapy.

According to a further aspect of the present invention there is provided a combination product comprising two or more fractions of doses of ZD6126 or a pharmaceutically acceptable salt thereof, which together add up to a total daily dose, for administration in divided doses, and a taxane, for use in a method of treatment of a human or animal body by therapy.

According to a further aspect of the present invention there is provided a kit comprising two or more fractions of doses of ZD6126 or a pharmaceutically acceptable salt thereof, which together add up to a total daily dose, for administration in divided doses, and one of: a platinum anti-tumour agent and a taxane.

According to a further aspect of the present invention there is provided a kit comprising two or more fractions of doses of ZD6126 or a pharmaceutically acceptable salt thereof, which together add up to a total daily dose, for administration in divided doses, and a platinum anti-tumour agent.

According to a further aspect of the present invention there is provided a kit comprising two or more fractions of doses of ZD6126 or a pharmaceutically acceptable salt thereof, which together add up to a total daily dose, for administration in divided doses, and a taxane.

According to a further aspect of the present invention there is provided a kit comprising:
a) two or more fractions of doses of ZD6126 or a pharmaceutically acceptable salt thereof, which together add up to a total daily dose, in first unit dosage forms for administration in divided doses;
b) one of: a platinum anti-tumour agent and a taxane in a second unit dosage form; and
c) container means for containing said first and second dosage forms.

According to a further aspect of the present invention there is provided a kit comprising:
a) two or more fractions of doses of ZD6126 or a pharmaceutically acceptable salt thereof, which together add up to a total daily dose, in first unit dosage forms for administration in divided doses;
b) a platinum anti-tumour agent in a second unit dosage form; and
c) container means for containing said first and second dosage forms.

According to a further aspect of the present invention there is provided a kit comprising:
a) two or more fractions of doses of ZD6126 or a pharmaceutically acceptable salt thereof, which together add up to a total daily dose, in first unit dosage forms for administration in divided doses;
b) a taxane in a second unit dosage form; and
c) container means for containing said first and second dosage forms.

According to a further aspect of the present invention there is provided a kit comprising:
a) two or more fractions of doses of ZD6126 or a pharmaceutically acceptable salt thereof, which together add up to a total daily dose, together with a pharmaceutically acceptable excipient or carrier, in first unit dosage forms for administration in divided doses;
b) one of: a platinum anti-tumour agent and a taxane, together with a pharmaceutically acceptable excipient or carrier, in a second unit dosage form; and
c) container means for containing said first and second dosage forms.

According to a further aspect of the present invention there is provided a kit comprising:
a) two or more fractions of doses of ZD6126 or a pharmaceutically acceptable salt thereof, which together add up to a total daily dose, together with a pharmaceutically acceptable excipient or carrier, in first unit dosage forms for administration in divided doses;
b) a platinum anti-tumour agent together with a pharmaceutically acceptable excipient or carrier, in a second unit dosage form; and
c) container means for containing said first and second dosage forms.

According to a further aspect of the present invention there is provided a kit comprising:
a) two or more fractions of doses of ZD6126 or a pharmaceutically acceptable salt thereof, which together add up to a total daily dose, together with a pharmaceutically acceptable excipient or carrier, in first unit dosage forms for administration in divided doses;
b) a taxane, together with a pharmaceutically acceptable excipient or carrier, in a second unit dosage form; and
c) container means for containing said first and second dosage forms.

According to a further aspect of the present invention there is provided the use of ZD6126 or a pharmaceutically acceptable salt thereof in the manufacture of a medicament for use when administered in divided doses in the production of a vascular damaging effect in a warm-blooded animal such as a human which is being treated with ionising radiation.

According to a further aspect of the present invention there is provided the use of ZD6126 or a pharmaceutically acceptable salt thereof in the manufacture of a medicament for use when administered in divided doses in the production of an anti-cancer effect in a warm-blooded animal such as a human which is being treated with ionising radiation.

According to a further aspect of the present invention there is provided the use of ZD6126 or a pharmaceutically acceptable salt thereof in the manufacture of a medicament for use when administered in divided doses in the production of an anti-tumour effect in a warm-blooded animal such as a human which is being treated with ionising radiation.

According to a further aspect of the present invention there is provided a combination treatment comprising the administration in divided doses of an effective amount of ZD6126 or a pharmaceutically acceptable salt thereof, optionally together with a pharmaceutically acceptable excipient or carrier, and the simultaneous, sequential or separate administration of an effective amount of one of:
  i) ionising radiation;
  ii) a platinum anti-tumour agent; and
  iii) a taxane;
wherein a platinum anti-tumour agent and a taxane may each optionally be administered together with a pharmaceutically acceptable excipient or carrier;
to a warm-blooded animal such as a human in need of such therapeutic treatment. Such therapeutic treatment includes a vascular damaging effect, an anti-cancer effect and an anti-tumour effect.

According to a further aspect of the present invention there is provided a combination treatment comprising the administration in divided doses of an effective amount of ZD6126 or a pharmaceutically acceptable salt thereof, optionally together with a pharmaceutically acceptable excipient or carrier, and the simultaneous, sequential or separate administration of an effective amount of ionising radiation to a warm-blooded animal such as a human in need of such therapeutic treatment.

According to a further aspect of the present invention there is provided a combination treatment comprising the administration in divided doses of an effective amount of ZD6126 or a pharmaceutically acceptable salt thereof, optionally together with a pharmaceutically acceptable excipient or carrier, and the simultaneous, sequential or separate administration of an effective amount of a platinum anti-tumour agent wherein said platinum anti-tumour agent may optionally be administered together with a pharmaceutically acceptable excipient or carrier, to a warm-blooded animal such as a human in need of such therapeutic treatment.

According to a further aspect of the present invention there is provided a combination treatment comprising the administration in divided doses of an effective amount of ZD6126 or a pharmaceutically acceptable salt thereof, optionally together with a pharmaceutically acceptable excipient or carrier, and the simultaneous, sequential or separate administration of an effective amount of a taxane wherein said taxane may optionally be administered together with a pharmaceutically acceptable excipient or carrier, to a warm-blooded animal such as a human in need of such therapeutic treatment.

As stated above the combination treatments of the present invention as defined herein are of interest for their vascular damaging effects. Such combination treatments of the invention are expected to be useful in the prophylaxis and treatment of a wide range of disease states where inappropriate angiogenesis occurs including cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation. In particular such combination treatments of the invention are expected to slow advantageously the growth of primary and recurrent solid tumours of, for example, the colon, breast, prostate, lungs and skin.

A combination treatment of the present invention as defined herein may be achieved by way of the simultaneous, sequential or separate administration of the individual components of said treatment. A combination treatment as defined herein may be applied as a sole therapy or may involve surgery, in addition to a combination treatment of the invention. Surgery may comprise the step of partial or complete tumour resection, prior to, during or after the administration of the combination treatment with ZD6126 described herein.

The compositions described herein may be in a form suitable for oral administration, for example as a tablet or capsule, for nasal administration or administration by inhalation, for example as a powder or solution, for parenteral injection (including intravenous, subcutaneous, intramuscular, intravascular or infusion) for example as a sterile solution, suspension or emulsion, for topical administration for example as an ointment or cream, for rectal administration for example as a suppository or the route of administration may be by direct injection into the tumour or by regional delivery or by local delivery. In other embodiments of the present invention the ZD6126 of the combination treatment may be delivered endoscopically, intratracheally, intralesionally, percutaneously, intravenously, subcutaneously, intraperitoneally or intratumourally. In general the compositions described herein may be prepared in a conventional manner using conventional excipients. The compositions of the present invention are advantageously presented in unit dosage form.

ZD6126 will normally be administered to a warm-blooded animal at a unit dose within the range 10–500 mg per square metre body area of the animal, for example approximately 0.3–15 mg/kg in a human. A unit dose in the range, for example, 0.3–15 mg/kg, preferably 0.5–5 mg/kg is envisaged and this is normally a therapeutically-effective dose. A unit dosage form such as a tablet or capsule will usually contain, for example 25–250 mg of active ingredient. Preferably a daily dose in the range of 0.5–5 mg/kg is employed.

Divided doses, also called split doses, means that the total dose to be administered to a warm-blooded animal, such as a human, in any one day period (for example one 24 hour period from midnight to midnight) is divided up into two or more fractions of the total dose and these fractions are administered with a time period between each fraction of about greater than 0 hours to about 10 hours, preferably about 1 hour to about 6 hours, more preferably about 2 hours to about 4 hours. The fractions of total dose may be about equal or unequal. Preferably the total dose is divided into two parts which may be about equal or unequal.

The time intervals between doses may be for example selected from:
about 1 hour, about 1.5 hours, about 2 hours, about 2.5 hours, about 3 hours, about 3.5 hours, about 4 hours, about 4.5 hours, about 5 hours, about 5.5 hours and about 6 hours.

The time intervals between doses may be any number (including non-integers) of minutes between greater than 0 minutes and 600 minutes, preferably between 45 and 375 minutes inclusive. If more than two doses are administered the time intervals between each dose may be about equal or unequal.

Preferably two doses are given with a time interval in between them of greater than or equal to 1 hour and less than 6 hours.

More preferably two doses are given with a time interval in between them of greater than or equal to two hours and less than 5 hours.

Yet more preferably two doses are given with a time interval in between them of greater than or equal to two hours and less than or equal to 4 hours.

Particularly the total dose is divided into two parts which may be about equal or unequal with a time interval between doses of greater than or equal to about two hours and less than or equal to about 4 hours.

More particularly the total dose is divided into two parts which may be about equal with a time interval between doses of greater than or equal to two hours and less than or equal to 4 hours.

For the avoidance of doubt the term 'about' in the description of time periods means the time given plus or minus 15 minutes, thus for example about 1 hour means 45 to 75 minutes, about 1.5 hours means 75 to 105 minutes. Elsewhere the term 'about' has its usual dictionary meaning.

Platinum anti-tumour agents include cisplatin, carboplatin, oxaliplatin and (SP-4-3)-(cis-amminedichloro[2-methylpyridine] platinum(II), otherwise known as ZD0473.

Taxanes include paclitaxel and docetaxel.

Platinum anti-tumour agents and taxanes may be dosed according to known routes of administration and dosages.

For example cisplatin may be administered as a single intravenous infusion over a period of 6–8 hours at a dose of 40–120 mg/m$^2$ every 3–4 weeks. Alternatively for example cisplatin may be administered as a single intravenous infusion over a period of 6–8 hours at a dose of 15–20 mg/m$^2$ daily for up to 5 days every 3–4 weeks.

For example carboplatin may be administered as a single short-term intravenous infusion over a period of 15–60 minutes at a dose of 250–400 mg/m$^2$ every 4 weeks.

For example oxaliplatin may be administered by intravenous infusion over a period of 2–6 hours at a dose of about 85 mg/m$^2$ every 2 weeks.

For example paclitaxel may be administered as an infusion over a period of about 24 hours at a dose of 135–200 mg/m$^2$ every 3 weeks. Alternatively for example paclitaxel may be administered as an infusion over a period of about 3 hours at a dose of 135–225 mg/m$^2$ every 3 weeks. Alternatively for example paclitaxel may be administered as an infusion over a period of about 1 hour at a dose of 80–100 mg/m$^2$ every week for a number of weeks. Alternatively for example paclitaxel may be administered as an infusion over a period of about 1 hour at a dose of 200 mg/m$^2$ every 3 weeks. Alternatively for example paclitaxel may be administered as an infusion over a period of about 96 hours at a dose of 120–140 mg/m$^2$ every 3 weeks.

Docetaxel may be dosed in according with known routes of administration and dosages. For example docetaxel may be administered as an infusion over a period of 1 hour at a dose of 55–100 mg/m$^2$ every 3 weeks.

In particular embodiments of the present invention the ionising radiation employed may be X-radiation, γ-radiation or β-radiation.

The dosages of ionising radiation will be those known for use in clinical radiotherapy. The radiation therapy used will include for example the use of γ-rays, X-rays, and/or the directed delivery of radiation from radioisotopes. Other forms of DNA damaging factors are also included in the present invention such as microwaves and UV-irradiation. It is most likely that all of these factors effect a broad range of damage on DNA, on the precursors of DNA, on the replication and repair of DNA and on the assembly and maintenance of chromosomes. For example X-rays may be dosed in daily doses of 1.8–2.0 Gy, 5 days a week for 5–6 weeks. Normally a total fractionated dose will lie in the range 45–60 Gy. Single larger doses, for example 5–10 Gy may be administered as part of a course of radiotherapy. Single doses may be administered intraoperatively. Hyperfractionated radiotherapy may be used whereby small doses of X-rays are administered regularly over a period of time, for example 0.1 Gy per hour over a number of days. Dosage ranges for radioisotopes vary widely, and depend on the half-life of the isotope, the strength and type of radiation emitted, and on the uptake by cells.

As stated above the size of the dose of each therapy which is required for the therapeutic or prophylactic treatment of a particular disease state will necessarily be varied depending on the host treated, the route of administration and the severity of the illness being treated. Accordingly the optimum dosage may be determined by the practitioner who is treating any particular patient. For example, it may be necessary or desirable to reduce the above-mentioned doses of the components of the combination treatments in order to reduce toxicity.

The present invention relates to combinations of ionising radiation, cisplatin or paclitaxel or docetaxel with ZD6126 or with a salt of ZD6126. Salts for use in pharmaceutical compositions will be pharmaceutically acceptable salts, but other salts may be useful in the production of ZD6126 and its pharmaceutically acceptable salts. Such salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

ZD6126 may be made according to the following process.

N-Acetylcolchinol (30.0 g, 83.9 mmol) is dissolved in acetonitrile under an inert atmosphere and 1,2,3-triazole (14.67 g, 212.4 mmol) added via a syringe. Di-tert-butyl-diethylphosphoramidite (37.7 g, 151.4 mmol) is added and the reaction mixture stirred at about 20° C. to complete the formation of the intermediate phosphite ester. Cumene hydroperoxide (24.4 g, 159.2 mmol) is added at about 10° C. and the reaction mixture stirred until the oxidation is complete. Butyl acetate (50 ml) and sodium hydroxide solution (250 ml of 1M) are added, the reaction mixture stirred and the aqueous phase discarded. The organic solution is washed with sodium hydroxide solution (2×250 ml of 1M) and a saturated solution of sodium chloride. Trifluoroacetic acid (95.3 g, 836 mmol) is added at about 15° C. The reaction mixture is distilled at atmospheric pressure, ZD6126 crystallises and is isolated at ambient temperature.

The following tests were used to demonstrate the activity of ZD6126 in combination with cisplatin, paclitaxel or ionising radiation.

ZD6126 in Combination with Cisplatin a) CaNT Tumour Model

In the murine adenocarcinoma CaNT tumour model grown in female CBA mice (Hill, S. A et al, Int. J. Cancer 63, 119–123, 1995) combining ZD6126 and cisplatin resulted in significantly improved growth delay compared to either agent alone.

(i) First Study

ZD6126 alone was dosed on days 0, 2 and 4 using a split dose regimen of 100 mg/kg ZD6126, followed by a 2 hour interval, followed by a further 100 mg/kg ZD6126; doses were given intraperitoneally (i.p.).

Cisplatin (David Bull Laboratories) alone was dosed at 5 mg/kg i.p on day 0.

The combination treatment consisted of:

Day 0: ZD6126 100 mg/kg i.p., followed by a 2 hour interval, followed by a further 100 mg/kg ZD6126 i.p; and cisplatin 5 mg/kg given 10 minutes before first ZD6126 dose.

Days 2 and 4: ZD6126 100 mg/kg i.p., followed by a 2 hour interval, followed by a further 100 mg/kg ZD6126 i.p.

The time for tumours to increase their geometric mean tumour diameter, measured in 3 directions, by 3 mm was calculated and is shown in Table 1 and the data displayed in FIG. 1.

TABLE 1

Anti-tumour activity of ZD6126 and cisplatin in CaNT tumours-study 1

| Treatment | Time to increase mean diameter by 3 mm (days) | Mean growth delay (vs control) - days |
|---|---|---|
| Control | 8.4, 8.2, 4.7, 7.2, 5.9 | — |
| Cisplatin alone | 10.0, 6.9, 9.2, 9.8 | 2.1 |
| ZD6126 alone | 16.4, 11.8, 11.6, 13.8 | 6.5 |
| Cisplatin plus ZD6126 | 17.8, 16.1, 20.1, 19.3, 19.3 | 11.6 |

The tumour growth delay caused by the combination of ZD6126 and cisplatin was significantly (Mann-Whitney U-test) greater than either cisplatin alone (P<0.01) or ZD6126 alone (P<0.05). The growth delay from the combination was greater than the sum of the growth delays from the individual treatments.

(ii) Second Study

ZD6126 alone was dosed on days 0, 4, 7 and 11 using a split dose regimen of ZD6126 100 mg/kg i.p., followed by a 2 hour interval, followed by a further 100 mg/kg ZD6126 i.p.. Cisplatin alone was dosed at 5 mg/kg i.p on day 0 and day 7.

The combination treatment consisted of:

Days 0 and 7: ZD6126 100 mg/kg i.p., followed by a 2 hour interval, followed by a further 100 mg/kg ZD6126 i.p.; cisplatin given 10 minutes before first ZD6126 dose.

Days 3, 7 and 10: ZD6126 100 mg/kg i.p., followed by a 2 hour interval, followed by a further 100 mg/kg ZD6126 i.p..

Figure 2:
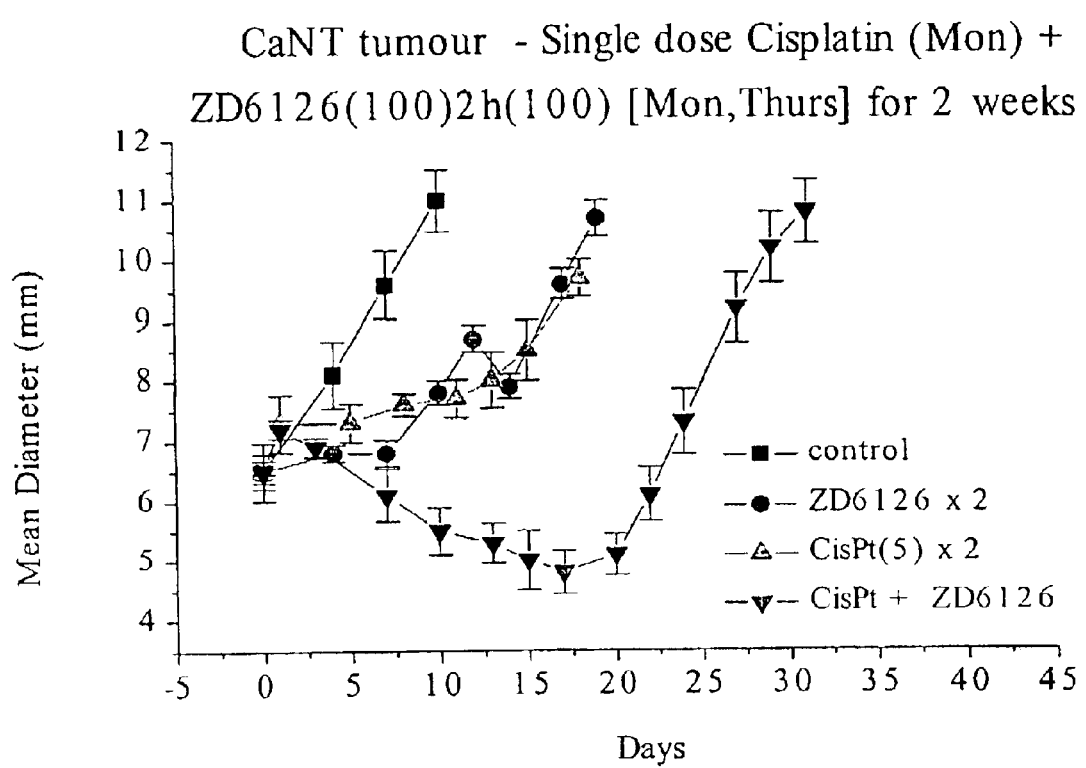

The time for tumours to increase their geometric mean tumour diameter, measured in 3 directions, by 3 mm was calculated and is shown in Table 2 and the data displayed in FIG. 2.

TABLE 2

Anti-tumour activity of ZD6126 and cisplatin in CaNT tumours-Study 2

| Treatment | Time to increase mean diameter by 3 mm (days) | Mean growth delay (vs control) - days |
|---|---|---|
| Control | 8.4, 8.2, 4.7, 7.2, 5.9 | — |
| Cisplatin alone | 15.7, 13.4, 12.5, 16.9 | 7.7 |
| ZD6126 alone | 16.4, 15.4, 17.8, 18.0, 16.5 | 9.9 |
| Cisplatin plus ZD6126 | 27.4, 24.3, 30.6, 26.7, 29.9 | 20.9 |

The tumour growth delay caused by the combination of ZD6126 and cisplatin was significantly greater than either cisplatin alone (P<0.01) or ZD6126 alone (P<0.01).

The growth delay from the combination was greater than the sum of the growth delays from the individual treatments.

b) Calu 6 Tumour Model

In a second tumour model, Calu 6, the advantage of combining ZD6126 and cisplatin (cis-Platinum(II) Diammine Dichloride—Sigma P-4394) was confirmed. Athymic nude mice were implanted subcutaneously with $1 \times 10^6$ human Calu 6 tumour cells (obtained from American Type Culture Collection, 10801 University Boulevard, Manassas, Va. 20110-2209 Cat. no. HTB-56) and tumours allowed to grow until they were approximately 9 mm in diameter.

Groups of 10 tumour bearing mice were then treated as follows:

ZD6126 alone was dosed 100 mg/kg i.p. on days 0, 1, 2, 3, 4.

Cisplatin alone was dosed 4 mg/kg i.p. on day 0.

Figure 3:
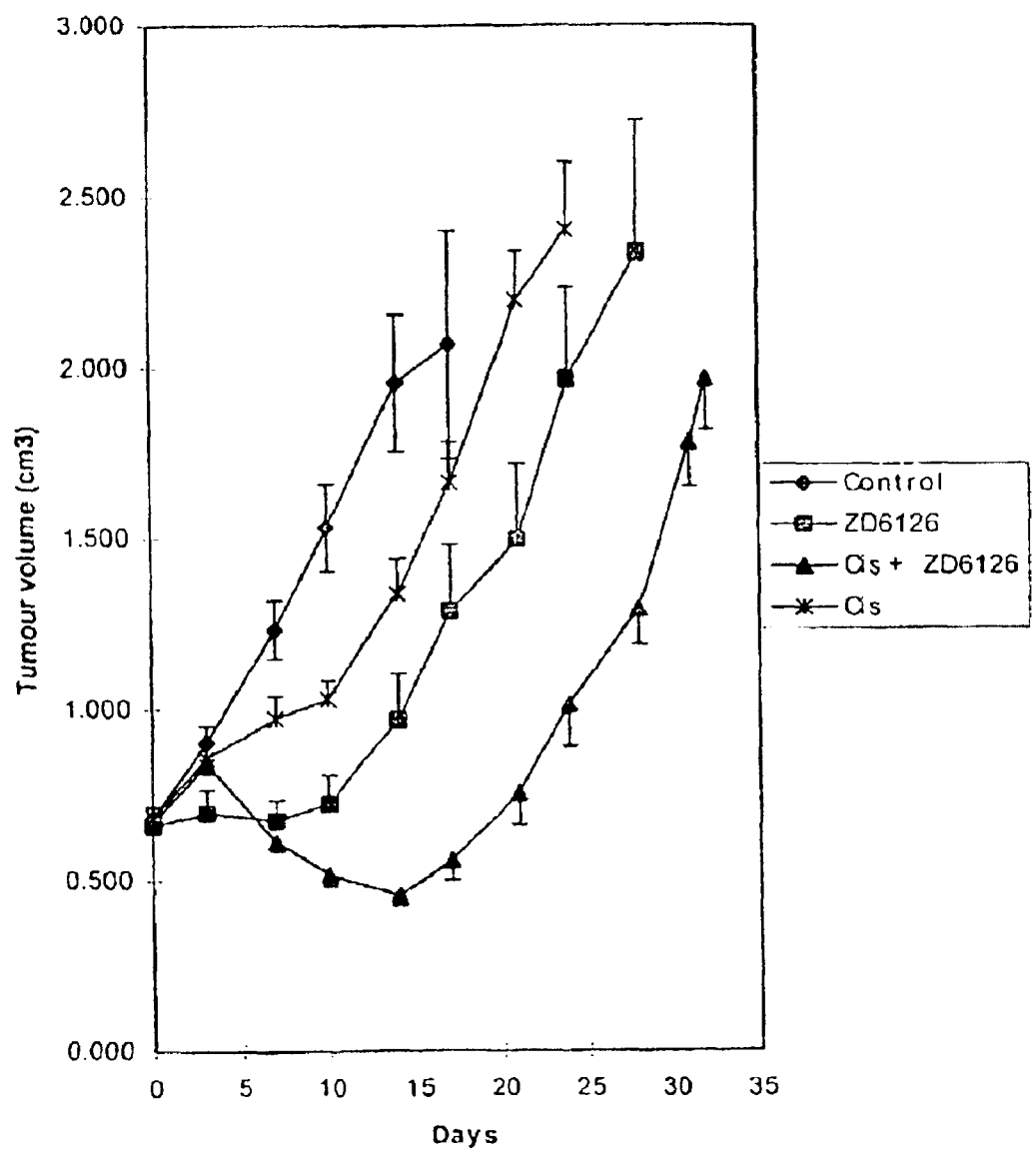

In the combination arm cisplatin 4 mg/kg i.p. was dosed on day 0, and ZD6126 100 mg/kg i.p. was dosed on days 1, 2, 3, 4 and 5. The results are shown in FIG. 3.

The combination of cisplatin and ZD6126 gave a growth delay (time to reach 2× starting volume) of 20.5 days compared to control tumours. This delay was significantly (p<0.05-Mann-Whitney U-test) longer than either ZD6126 alone (10.1 days) or cisplatin alone (6.0 days). The growth delay from the combination was greater than the sum of the growth delays from the individual treatments.

c) KHT Sarcoma Tumour Model

Figure 4:
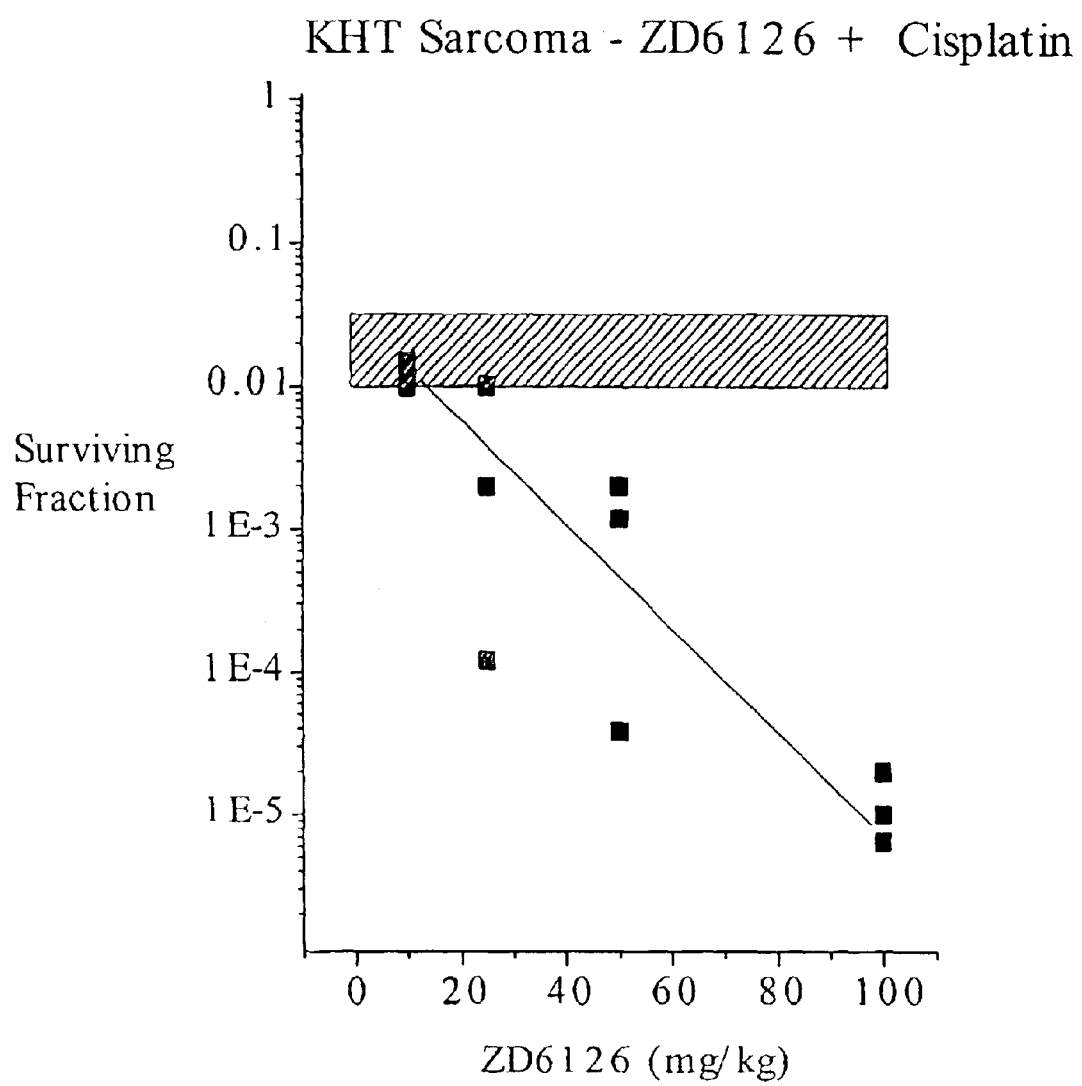

In the murine KHT sarcoma model (Lingyun Li, B. S. et al, Int. J. Radiation Oncology Biol. Phys 42, 899–903, 1998) tumours were treated with either 10 mg/kg cisplatin i.p. alone or 10 mg/kg cisplatin plus ZD6126 (10–100 mg/kg i.p.), cisplatin given 1 hour prior to ZD6126. The effects of the treatments on tumour cell survival was assessed 24 hours later by excising the tumour, disaggregating the cells and determining the number of colonies formed after 10–14 days. Surviving fraction compared to untreated cells was then determined. The results are shown in FIG. 4.

Cisplatin alone resulted in approximately 98% cell killing (hatched area in FIG. 4) and this effect was enhanced in a dose dependent fashion with ZD6126.

The mean percent cell survival at 20, 50 and 100 mg/kg was 0.4, 0.011 and 0.0012% respectively and thus these doses enhanced cell kill over cisplatin alone by 5, 182 and 1667 fold respectively.

ZD6126 in Combination with Ionising Radiation a) CaNT Tumour Model

The activity of combining ZD6126 and radiation in the CaNT tumour model was also investigated. Tumours were treated with either radiation alone (15 Gy days 0 and 7), ZD6126 alone (single dose of ZD6126 125 mg/kg i.p. on days 0, 1, 2, 3, 4, 7, 8, 9, 10 and 11), or a combination of both (15 Gy days 0 and 7, ZD6126 125 mg/kg i.p. on days 0, 1, 2, 3, 4, 7, 8, 9, 10 and 11). On the days radiation and ZD6126 were administered together, radiation treatment was given 3 hours after ZD6126 administration. Radiation was administered by placing the mice in lead boxes so that only the tumour bearing portion of the rear dorsum was exposed to a horizontal X-ray beam (Sheldon and Hill, BJC, 35, 795–808, 1997). Mice were irradiated with 240 kV X-rays at a dose rate of 3.6 Gy/min.

Figure 5:
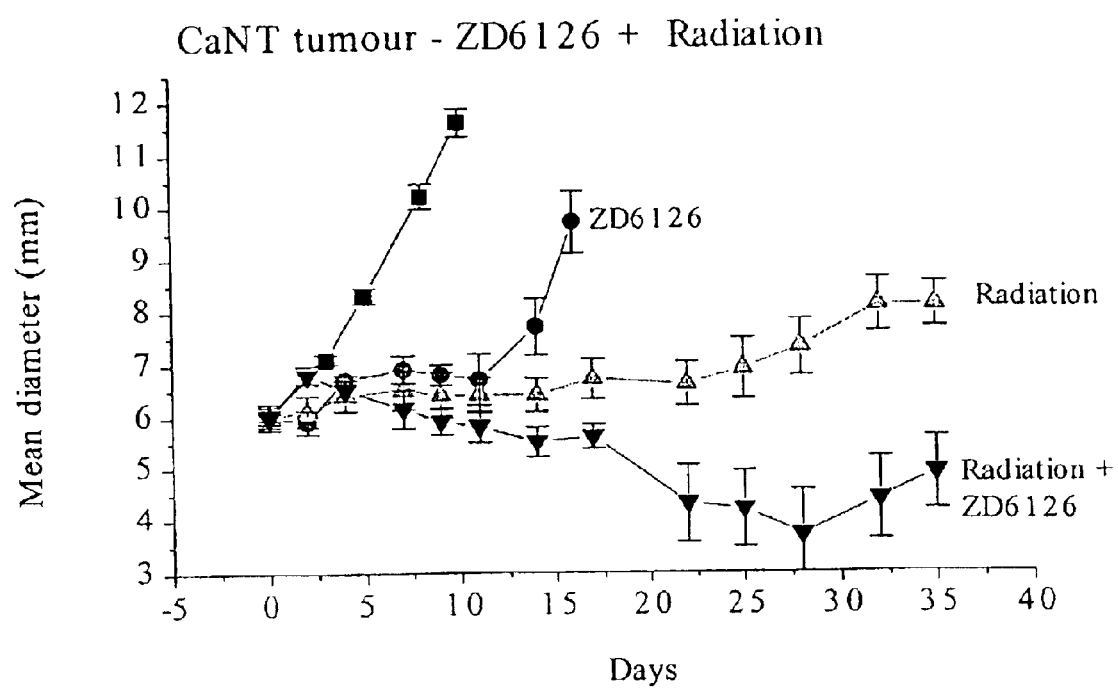

The time for tumours to increase their geometric mean tumour diameter, measured in 3 directions, by 3mm was calculated and is shown in Table 3 and the data displayed in FIG. 5.

TABLE 3

Anti-tumour effects of ZD6126 and radiation in CaNT tumours

| Treatment | Time to increase mean diameter by 3 mm (days) | Mean growth delay (vs control)-days |
|---|---|---|
| Control | 6.0, 8.0, 6.7, 5.1, 6.3, 6.6, 5.1, 6.4 | — |
| Radiation alone | 47.3, 53.0, 31.5, 54.3, 37.0 | 38.3 |
| ZD6126 alone | 15.6, 17.7, 14.1, 14.6, 14.7 | 9.1 |
| Radiation and ZD6126 | 49.0, 58.0, 57.5, 63.5, 55.6 | 50.4 |

The tumour growth delay caused by the combination of ZD6126 and radiation was significantly greater than either radiation alone (P<0.05) or ZD6126 alone (P<0.01). The growth delay from the combination was greater than the sum of the growth delays from the individual treatments.

b) KHT Sarcoma Tumour Model

Figure 6:
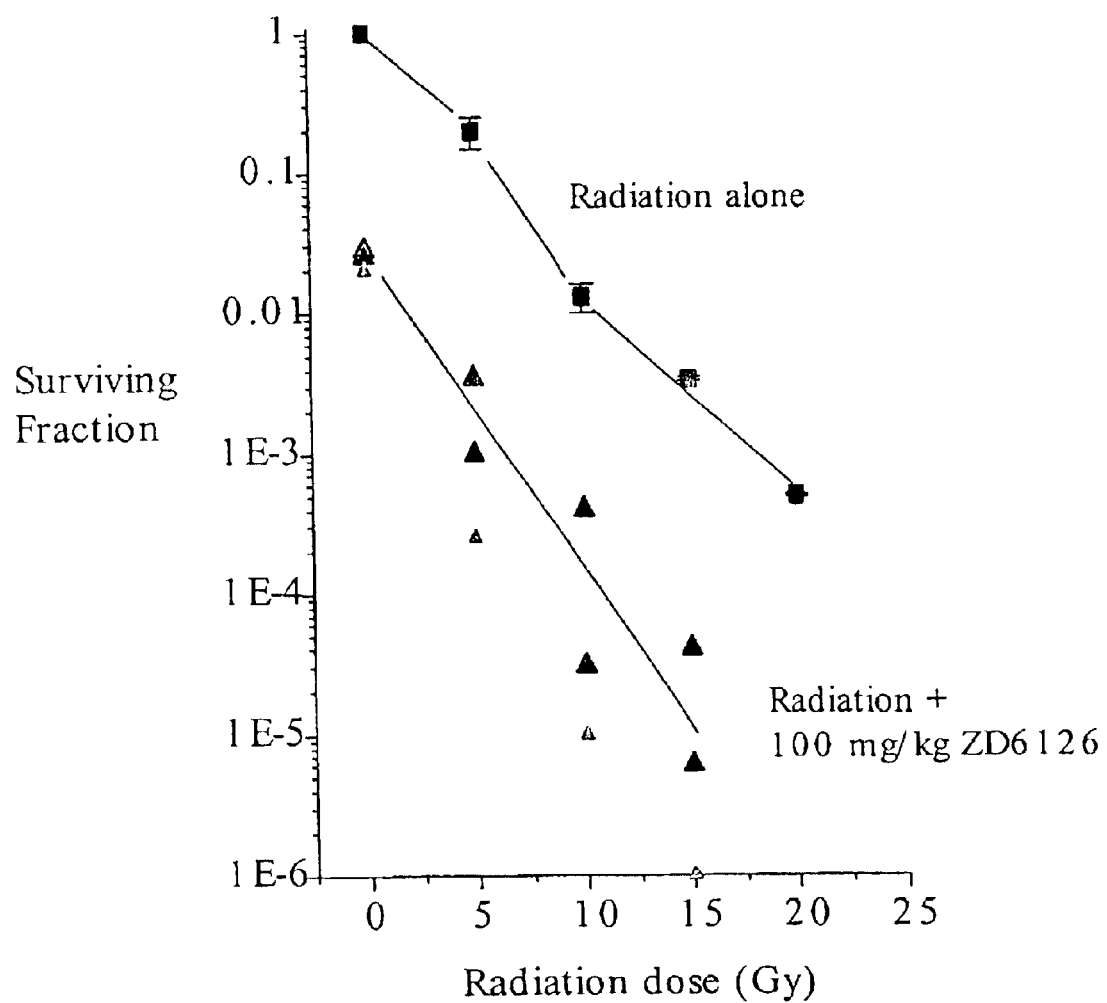

The murine KHT sarcoma grown in C3H mice was also used to confirm the advantage of combining ZD6126 and radiation. Tumours were treated with either radiation alone (0, 5, 10, 15 or 20 Gy single dose), ZD6126 100 mg/kg i.p., or radiation followed 1 hour later by ZD6126 100 mg/kg i.p.. The effects of either radiation alone, ZD6126 alone or the combination on tumour cell survival was assessed 24 hours later by excising the tumour, disaggregating the cells and determining the number of colonies formed after 10–14 days. Surviving fraction compared to untreated cells was then determined. The results are shown in FIG. 6.

ZD6126 alone (100 mg/kg) killed approximately 97–98% of the tumour cells and enhanced the level of tumour killing at all 3 radiation doses tested. Combining ZD6126 with radiation doses of 5, 10 or 15 Gy result in 100–200 fold enhancement in cell killing (ZD6126 alone with no radiation enhanced cell killing by 40 fold over controls)—Table 4.

TABLE 4

Anti-tumour effects of ZD6126 and radiation in KHT Sarcoma

| Radiation dose(Gy) | % cell survival | Plus ZD6126 % cell survival | ZD6126 Enhancement |
|---|---|---|---|
| 0 | 100 | 2.5 | 40 |
| 5 | 20 | 0.16 | 125 |
| 10 | 15 | 0.015 | 100 |
| 15 | 0.35 | 0.0016 | 219 |
| 20 | 0.05 | ND | — |

ND = not determined

ZD6126 in Combination with Paclitaxel a) FaDu Tumour Model

In a third tumour model $5 \times 10^5$ FaDu cells (human squamous cell carcinoma of the pharynx) were implanted onto the rear dorsum of 12-16 week old, female SCID mice. When the tumours had become established they were excised and cut into small tumour fragments approximately 1 mm$^3$. These fragments were implanted subcutaneously into further SCID mice. Once these tumours had become established (approximately 6 mm diameter) mice were treated with either a single dose of ZD6126 (125 mg/kg i.p.) alone, a single dose of paclitaxel (Taxol-BMS) (15 or 30 mg/kg i.p.) alone or the combination of a single dose of paclitaxel (15 mg/kg i.p.) and ZD6126 (125 mg/kg i.p.), paclitaxel being given 15 minutes before ZD6126.

Figure 7:
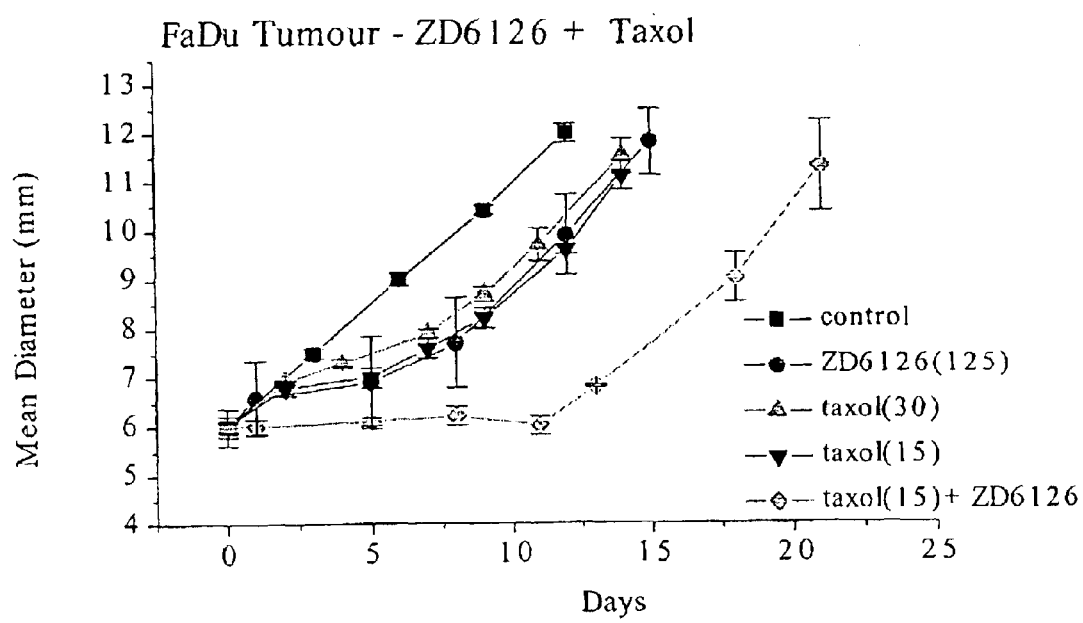

The time for tumours to increase their geometric mean tumour diameter, measured in 3 directions, by 3 mm was calculated and is shown in Table 5 and the data displayed in FIG. 7.

TABLE 5

Anti-tumour effects of ZD6126 and Paclitaxel in FaDu tumours

| Treatment | Time to increase mean diameter by 3 mm (days) | Mean growth delay (vs control)-days |
|---|---|---|
| Control | 6.0, 5.0, 5.0, 5.4, 5.8, 7.0, 6.8, 5.2, 6.8 | — |
| Paclitaxel (15 mg/kg) alone | 11.2, 10.8 | 5.1 |
| ZD6126 alone | 8.9, 12.5, 12.0, 7.3 | 4.3 |
| Paclitaxel plus ZD6126 | 22.4, 19.6, 18.1 | 14.1 |

The tumour growth delay caused by the combination of ZD6126 and paclitaxel was significantly greater than giving ZD6126 alone (P<0.05). The growth delay from the combination was greater than the sum of the growth delays from the individual treatments.

Cell Survival Assay

The activity of ZD6126 administered in split doses may be demonstrated by the following cell survival assay.

In vivo cell survival was measured using an excision assay (D J Chaplin et al., Anticancer Research 19: 189–196 (1999)).

For each of the assays a) and b) below, the surviving fraction of tumour cells was determined as follows:

Tumours were excised at about 18 hours after treatment, weighed and disaggregated for 1 hour at 37 degrees Celsius in an enzyme cocktail containing 1 mg/ml pronase, 0.5 mg/ml DNAase and 0.5 mg/ml collagenase. Haemocytometer counts of trypan blue-excluding cells were made and viable cells seeded in appropriate concentrations to yield about 50 colonies/dish after in vitro incubation. Heavily irradiated feeder cells (V79 cells) were used at a concentration of 25,000/ml to support the growth of the surviving CaNT cells. The data were calculated as surviving fraction per gram of tumour.

a) CaNT Tumour Model: Effect of Dosage Interval

Figure 8:
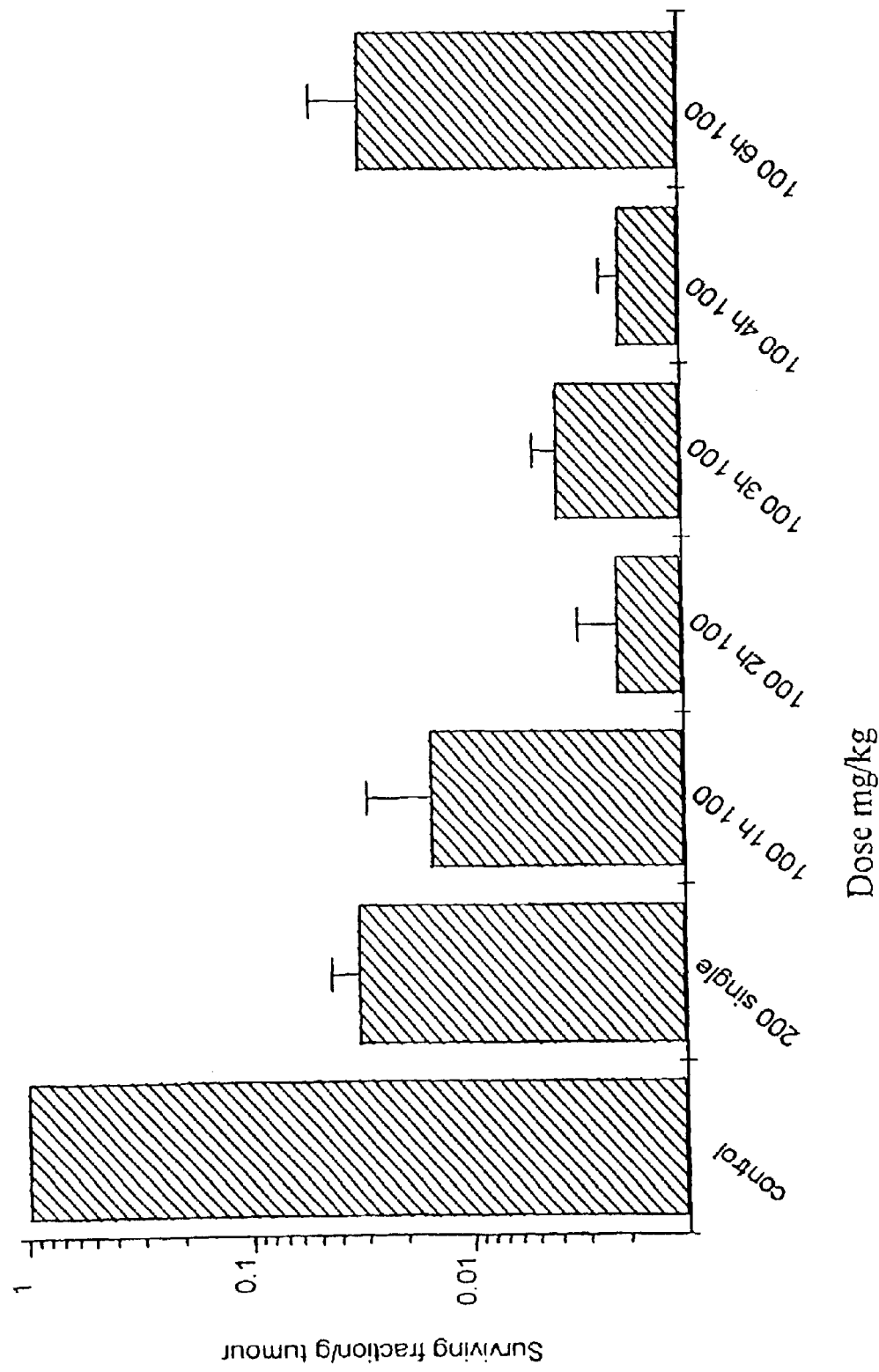

In the murine adenocarcinoma CaNT tumour model grown in female CBA mice (Hill, S. A et al, Int. J. Cancer 63, 119–123, 1995) administering ZD6126 in divided doses resulted in an improved anti-tumour effect compared to ZD6126 administered as a single dose as measured by surviving fraction of tumour cells. See FIG. 8.

Methodology

Single Dose

ZD6126 was administered as a single dose of 200 mg intra-peritoneally (i.p.) in saline with a small amount of 1% sodium carbonate added to aid the dissolution of ZD6126.

Divided Doses

ZD6126 was dosed using a split dose regimen of 100 mg/kg ZD6126, followed by a time interval, followed by a further 100 mg/kg ZD6126; doses were given intraperitoneally (i.p.) in saline with a small amount of 1% sodium carbonate added to aid the dissolution of ZD6126. The time intervals used were 1, 2, 3, 4 and 6 hours.

Surviving fraction per gram of tumour was determined as described above and plotted as shown in FIG. 8.

Two doses of 100 mg/kg separated by 2, 3 or 4 hours were significantly more effective in this model than a single 200 mg/kg dose.

b) CaNT Tumour Model: Effect of Dosage Interval and Split Dose Proportions

Figure 9:
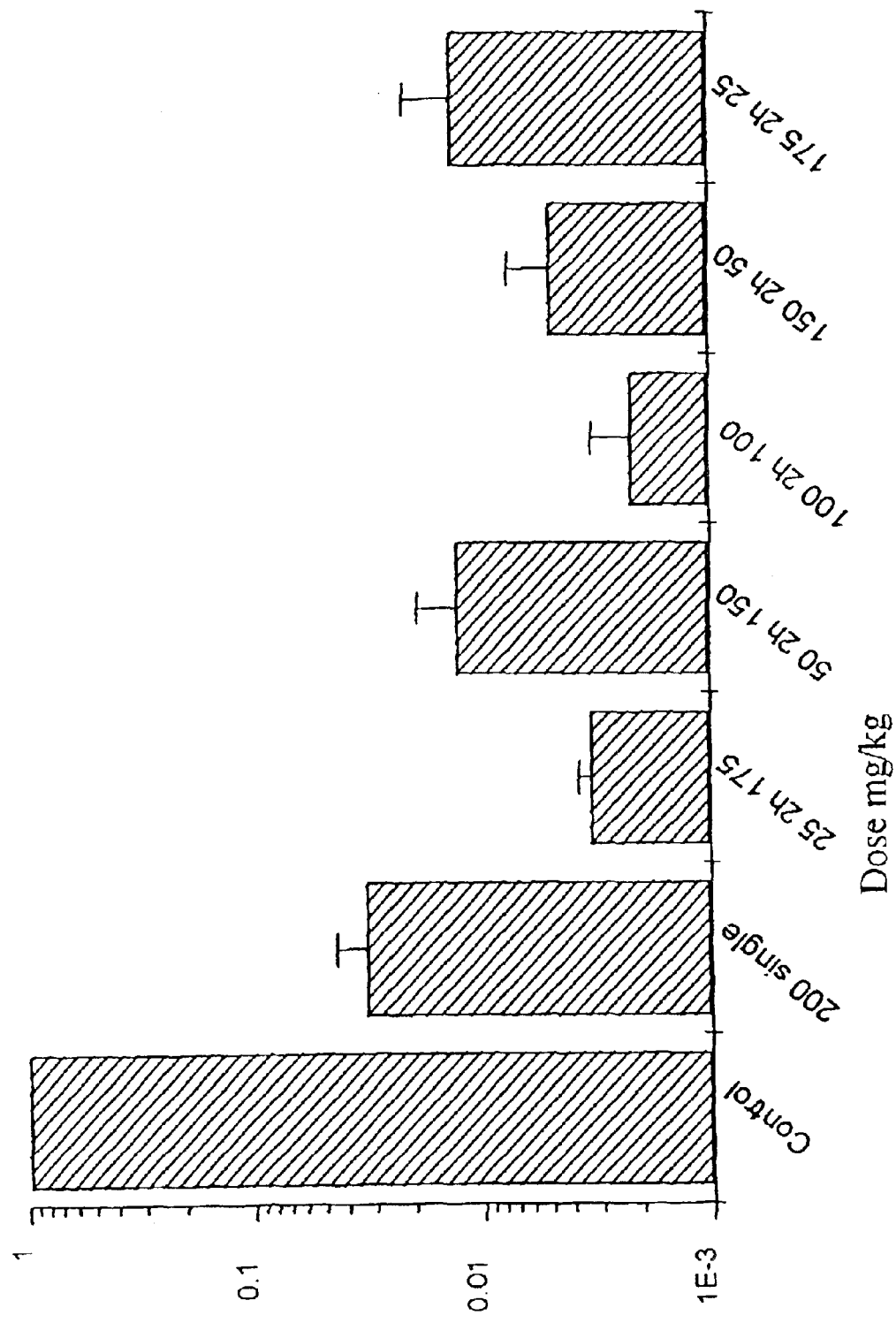

In the murine adenocarcinoma CaNT tumour model grown in female CBA mice (Hill, S. A et al, Int. J. Cancer 63, 119–123, 1995) administering ZD6126 in divided doses 2 hours apart resulted in an improved anti-tumour effect, as measured by surviving tumour cell fraction, compared to ZD6126 administered as a single dose. This improved effect varied with the proportion of total dose given in the first and second doses. See FIG. 9.

Methodology

Single Dose

ZD6126 was administered as a single dose of 200 mg intra-peritoneally (i.p.) in saline with a small amount of 1% sodium carbonate added to aid the dissolution of ZD6126.

Divided Doses

ZD6126 was dosed using split dose regimens of:
i) 25 mg/kg ZD6126, followed by a 2 hour interval, followed by a further 175 mg/kg ZD6126;
ii) 50 mg/kg ZD6126, followed by a 2 hour interval, followed by a further 150 mg/kg ZD6126;
iii) 100 mg/kg ZD6126, followed by a 2 hour interval, followed by a further 100 mg/kg ZD6126;
iv) 150 mg/kg ZD6126, followed by a 2 hour interval, followed by a further 50 mg/kg ZD6126;
v) 175 mg/kg ZD6126, followed by a 2 hour interval, followed by a further 25 mg/kg ZD6126; All doses were given intraperitoneally (i.p.) in saline with a small amount of 1% sodium carbonate added to aid the dissolution of ZD6126.

The anti-tumour effect, as measured by surviving fraction of tumour cells, was greater with divided doses of ZD6126 than with a single dose of 200 mg/kg ZD6126. This greater effect was significant when divided doses of ZD6126 were administered according to i), iii) or iv) above. The best effect was seen with equal split doses, ie according to iii) above.

What is claimed is:

1. A pharmaceutical composition which comprises ZD6126

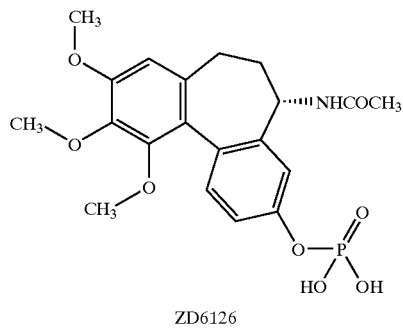

ZD6126 or a pharmaceutically acceptable salt thereof, and a platinum anti-tumour agent in association with a pharmaceutically acceptable excipient or carrier.

2. A pharmaceutical composition which comprises ZD6126 or a pharmaceutical acceptable salt thereof, and a taxane in association with a pharmaceutically acceptable excipient or carrier.

3. A kit comprising:
(a) ZD6126 or pharmaceutically acceptable salt thereof in a first unit dosage form;
(b) one of: a platinum anti-tumour agent and a taxane in a second unit dosage form; and
(c) container means for containing said first and second dosage forms.

4. A kit comprising;
(a) two or more first unit dosage forms of ZD6126 or a pharmaceutically acceptable salt thereof, which together comprise a total daily dose of ZD6126;
(b) one of: a platinum anti-tumour agent and a taxane in a second unit dosage form; and
(c) container means for containing said first and second dosage forms.

5. A kit comprising:
(a) ZD6126 or pharmaceutically acceptable salt thereof in a first unit dosage form;
(b) a platinum anti-tumour agent in a second unit dosage form; and
(c) container means for containing said first and second dosage forms.

6. A kit comprising:
(a) ZD6126 or pharmaceutically acceptable salt thereof in a first unit dosage form;
(b) a taxane in second unit dosage form; and
(c) container means for containing said first and second dosage forms.

7. A kit comprising:
(a) two or more first unit dosage forms of ZD6126 or a pharmaceutically acceptable salt thereof, which together comprise a total daily dose of ZD6126;
(b) a platinum anti-tumour agent in a second unit dosage form; and
(c) container means for containing said first and second dosage forms.

8. A kit comprising:
(a) two or more first unit dosage forms of ZD6126 or a pharmaceutically acceptable salt thereof, which together comprise a total daily dose of ZD6126;
(b) a taxane in second unit dosage form; and
(c) container means for containing said first and second dosage forms.

9. The kit according to claim 7 or claim 8 comprising two approximately equal first unit dosage forms of ZD6126, or a pharmaceutically acceptable salt thereof.

* * * * *